United States Patent [19]
Ravindranathan et al.

[11] Patent Number: 5,274,107
[45] Date of Patent: Dec. 28, 1993

[54] PROCESS FOR SYNTHESIS OF D(+) BIOTIN

[75] Inventors: Thottapillil Ravindranathan; Subhash P. Chavan; Rajkumar B. Tejwani, all of Maharashtra, India

[73] Assignee: Council of Scientific & Industrial Research, New Delhi, India

[21] Appl. No.: 863,794

[22] Filed: Apr. 6, 1992

[51] Int. Cl.$^5$ .......................................... C07D 495/04
[52] U.S. Cl. ................................................. 548/303.7
[58] Field of Search ........................... 548/303, 303.7

[56] References Cited

PUBLICATIONS

Y. Hashimoto K. Saigo, S. Michida, M-Hsegana Tetrahedron Letters, 1990, 31 p. 5625.
C-Yu Hsu; Y-S Lin; J-J Uang Tetrahderon Asymmetry 1990, 1, 219.
D. G. Melillo, R. D. Larsen, D. J. Mathre, W. R. Shukis, A. W. Wood, J. R. Colleluoric J. Org. Chem. 1987, 52, 5143.
R. E. Ireland, S. Thaisrivongs, N. Vanter, C. S. Wilcox J. Org. Chem. 1980, 45, 48.
Y. Taniguchi, J. Inanaga, M. Yamaguchi, Bull. Chem. Soc. Jpn. 1981, 54, 3229.
R. M. Williams, R. W. Armstrong, L. K. Maruyama, J. S. Dung, O. P. Anderson J. Amer. Chem. Soc. 1985, 107, 3246.
E. F. Klemman, 2, 893, I. Patterson 12, 301, H. B. Mekeiburge, C. S. Wilcox, 2, 99, H. Yamamoto 2, 81 Ed. B. M. Trost I. Fleming Pergamon Press, 1991 "Comprehensive Organic Synthesis".
A. Pelter, K. Smith and H. C. Brown, Borane Reagents, 1988, 1.
E. J. Corey and X-M Cheng The Logic of Chemical Synthesis, 1989, 100.
Ravindranathan et al., Synth. Comm., 18(15), pp. 1855-1861 (1988).

*Primary Examiner*—Joseph Paul Brust
*Assistant Examiner*—Mary Susan H. Gabilan
*Attorney, Agent, or Firm*—Ladas & Parry

[57] ABSTRACT

The invention discloses an improved process for the synthesis of D(+) biotin of the Formula

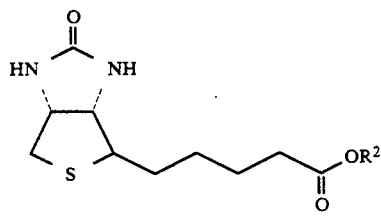

where $R^2$ represents hydrogen or methyl Biotin is one of the B-complex group of vitamins having immense commercial importance in the area of animal health and nutrition.

7 Claims, 1 Drawing Sheet

PROCESS FOR SYNTHESIS OF D(+) BIOTIN

This invention relates to an improved process for synthesis of D(+) biotin. Biotin (Vitamin H), is one of the B-complex group of vitamins has immense commercial importance, in the area of animal health and nutrition. It is one of the biocatalysts of the reversible metabolic reactions of carbon dioxide transport in micro and macro organisms. It is used in poultry feeds for rapid growth of chicks and healthy hatching of eggs. Biotin - avidin complex finds a vital role in the area of biochemistry. D(+) biotin prepared by the process of the present invention has the Formula I

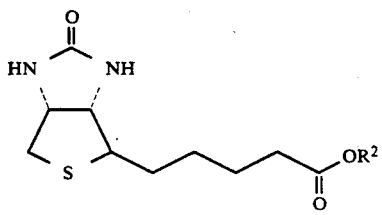

and as also shown in FIG. 1.

BACKGROUND OF THE INVENTION

It has hitherto been known to prepare (+) biotin from amino acids viz. cystine, cysteine and serine. Prior art processes involving L-cystine as the precursor incorporate intramolecular radical cyclization (E. J. Corey, M. M. Mehrotra Tetrahedron Letters 29, 57 (1988) as the key step to construct the tetrahydrothiophene moiety of biotin. Another prior art process revolves around intramolecular cycloaddition (3+2) of derivatives of L-cystine (E. G. Baggiolini, H. L. Lee, G. Pizzolato and M. R. Uskokovic, J. Amer. Chem. Soc., 104, 6460-6462 (1982), and L-cysteine (H. L. Lee, E. G. Baggiolini and M. R. Uskokovic, Tetrahedron, 43, 4887 (1987). In another process starting from L-cysteine, a bicyclic hydantoin is the key intermediate leading to D(+) biotin. E. Poetsch and M. Casutt, EP 242,686 (1986); CA 108: 112077K (1988); Chimia 41, 148-150 (1987). In a totally different and novel approach, L-cysteine was converted to its thiazolidine derivative which on treatment with bromine is converted stereospecifically to a bicyclic intermediate as a single stereoisomer and eventually transformed to D(+) biotin (P. N. Confalone, E. G., Baggiolini, D. Lollar, and M. R. Uskokovic, J. Amer. Chem. Soc., 99, 7020-7026 (1977).

Hitherto known processes involve highly toxic and hazardous chemicals e.g. phosgene for the formation of hydantoin. Moreover the intramolecular radical cyclization leads to both six as well as the desired five membered ring system along with tin inclusion compounds as the undesired by-products.

In another prior art process involving intramolecular 3+2 cycloaddition reaction of nitrone, the precursor olefin is obtained as a mixture (9:1) of which the desired olefin has to be purified and separated by chromatography. Moreover, the chiral intermediates obtained during the above mentioned sequence of reactions were prone to racemization.

Another prior art process involving the intramolecular cyclization of thiazolidine required Collins oxidation as one of the steps. Use of heavy metals on an industrial scale would lead to problems during waste disposal. Moreover, Wittig reaction, on the aldehyde leads to a mixture of isomers which should be separated and the desired isomer subjected to further reactions leading to biotin.

The following abreviations are used in this application:
TBDMSOTf: tert-Butyldimethylsilyl trifluoromethanesulfonate
TMSOTf: Trimethylsilyl trifluoromethanesulfonate
LDA: Lithium diisopropylamide
KOBut: Potassium tert-butoxide
AgOTf: Silver trifluoromethanesulfonate
TMSC1: Chlorotrimethylsilane
TBDMSC1: tert-Butyldimethylsilyl chloride
CSA: 10-Camphorsulfonic acid
Et$_3$N: Triethylamine
DIBAL: Diisobutylaluminium hydride
PTSA: para-Toluenesulphonic acid

BRIEF SUMMARY OF INVENTION

The main objective of the present invention is to synthesize D(+) biotin from substituted hydantoins of the Formula A of the accompanying drawings The optically pure hydantoin of the Formula A are prepared from racemic or optically pure chiral amino acids. Thus hydantoins of general Formula A are reduced to lactol of the Formula B of the drawings. The animal of the lactol of the Formula B is selectively protected wit thiophenol to furnish the thio aminal aldehyde of the Formula C of the drawings. The aldehyde of the Formula C is converted to its silylenol ether of the Formula D of the drawings. Cyclisation of ether of the Formula D is performed in methylene chloride in the presence of p-nitrobenzaldehyde using catalytic amount of TBDMSOTf/TMSOTf to furnish the tetrahydro thiophene aldehyde of the formula E of the drawings in high yields Witting olefination of the.aldehyde of the Formula E with (3-methoxycarbonyl-2-propenylidene) triphenylphos-phorane at room temperature furnished compound of the Formula F of the drawings in high yields Deconjugation of compound of the Formula F with LDA, KoBut, NaOMe, (NaOH or KOH) smoothly furnished the deconjugated ester (acid) of the formula G of the drawings in high yields Catalytic hydrogenation of compound of the Formula G using Pearlmans catalyst Pd(OH)$_2$ afforded compound of the Formula H of the drawings with all three stereocentres in cis-relationship. Deprotection of compound of the Formula H afforded (+)biotin of the Formula I. All the conditions employed in the process are mild, simple, efficient and of short duration.

DETAILED DESCRIPTION OF THE INVENTION

Figure 1:
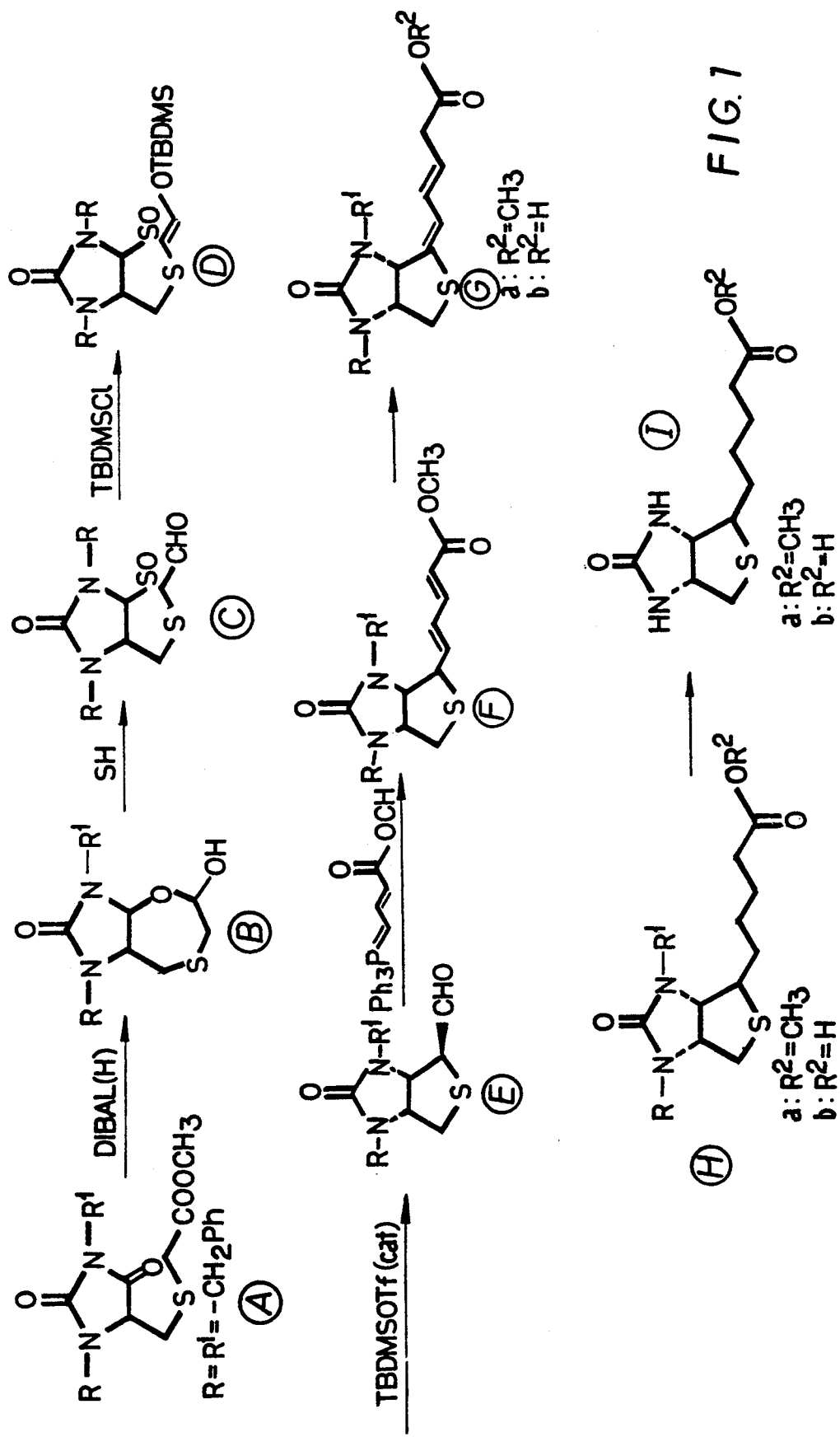
FIG. 1—illustrates the process for the synthesis of D(+) biotin.

Accordingly, the present invention provides an improved process for the synthesis of D(+) biotin of the Formula I shown in the drawing accompanying this specification which comprises:

(a) reducing by known methods, a hydantoin of the Formula A to the corresponding lactol of the Formula B, (b) selectively protecting the aminal of the Formula B with thiophenol to furnish the thio aminal aldehyde of the Formula C, (c) converting the aminal aldehyde of the Formula C to silyl enol ether of the Formula D by silation by known methods, (d) cyclising the ether of the Formula D in the presence of methylene chloride and p-nitro benzaldehyde employing Lewis acids such as $BF_3$, $EtO_2$, AgOAC, AgOTf, $SnCl_4$, $AlCl_3$, TmSoTf or TBDMSoTf as catalyst to furnish the tetra hydro thiophene aldehyde of the Formula E, (e) treating the aldehyde of the Formula E with 3 (methoxycarbonyl-2-propenylidene) triphenylphosphorane at room temperature to furnish compound of the Formula F, (f) deconjugating the compound of the Formula F with lithium NaOMe, NaOH, diisopropylamide, KoBut or KOH to furnish the deconjugated ester (acid) of the Formula G, (g) catalytically hydrogenating the compound of the Formula G using pearlmans catalyst $Pd(OH)_2$ to furnish the compound of the Formula H where $R^2$ represents hydrogen or methyl, (h) deprotecting the compound of the Formula H by conventional methods to yield the biotin of the Formula I where $R^2$ represents hydrogen or methyl.

Preferably according to the invention all the steps in the process of the present invention are carried out at room temperature.

The reduction of compound of the Formula A to compound of the Formula B may be effected by employing DIBAL.

The selective protection of compound of the Formula B may be effected by using PTSA, CSA and Benzene, Sulphonic acid.

The conversion of aminal aldehyde of the Formula C silyl enol ether of the Formula D is effected by employing TMSCl, TBDMS Cl, TBDMSOTf, Etzn and the like.

The deprotection of the compound of the Formula H is effected employing aqueous HBr or metal/$NH_3$.

The invention is described with reference to the following example which are given by way of illustration only and therefore should not be construed to limit the scope of the invention.

EXAMPLE 1

5,6-(1, 3-dibenzyl-2-ketoimidazolido)-3-hydroxy-1,4-oxathiepin compound of the Formula B A solution of R(+) 1,3 dibenzyl 1-5 (methoxycaronylmethylthiomethyl hydantoin of the Formula A 0.398 parts (1 mmol part) in dry toluene (10 parts) was added DIBAL-H 1.023 parts (2.2 mmol part) at −78° C. during 1 hr. The reaction mixture was stirred for additional 2 h and quenched by addition of methanol (5 parts). Filtration through celite and concentration of the solvent furnished a residue which on purification by column ($SiO_2$) using ethylacetate-pet ether (60%) as eluent afforded lactol of the Formula B in 0.266 parts (72%), $(\alpha)_D = +36.2$ c = 1.08 (MeOH).

EXAMPLE 2

2-imidazolidone-4-(formylmethylthiomethyl)-1, 3-dibenzyl-5-thiophenyl compound of the Formula C To a solution of 5,6-(1,3 dibenzyl-2-ketoimidazolido)-3-hydroxy-1,4-oxathiepin of the Formula B 0.370 parts (1 mmol part) in thiophenol (1 part) was added p-TSA (catalytic) at 0° C. The reaction mixture was stirred at 0° for 5 min. Water (2 parts) was added and extraction with dichloromethane and removal of solvent after drying (anhyd. $Na_2SO_4$) furnished a residue which on purification by chromatography ($SiO_2$) using ethylacetate-pet (20%) furnished the 2-imidazolidone-4-(formylmethylthiomethyl)-1,3-dibenzyl-5-thiophenyl of the formula C 0.323 parts (70%).

EXAMPLE 3

2-imidazolidone-4-(2-tert-butoxydimethylsilyloxy-1-ethenylthiomethyl) -1,3-dibenzyl-5-thiophenyl compound of the Formula D To a solution of aldehyde of the Formula C 0.576 parts (1 mmol part) in dry dichloromethane (10 parts) was added DBU 0.182 parts (1.2 mmol part). TBDMSCl 0.165 parts (1.1 mmol part) was introduced in the reaction and stirred for 2 h. Purification of the residue, obtained by removal of solvent, by chromatography ($SiO_2$) using 15% EtOAc-pet ether as eluent furnished the silyl enol ether of the Formula D 0.529 parts (92%).

EXAMPLE 4

3,4-(1,3-dibenzyl-2-ketoimidazolido)-2-formylthiophane of the Formula E

To a solution of enol ether (D) 0.576 parts (1 mmol part) and p-nitrobenzaldehyde 0.188 parts (1.25 mmol part) in dichloromethane (10 parts) was added TBSOTf (catalytic) at room temperature. After 10 min aq $NaHCO_3$ solution was added Extraction with dichloromethane and purification by chromatography ($SiC_2$) using ethylacetate-pet (60%) as the eluent gave the aldehyde (E) 0.316 parts (90%) $(\alpha)_D = -60$ c = 0.9 ($CHCl_3$).

EXAMPLE 5

3S, 4R-(1,3-dibenzyl-2-ketoimidazolido)-2R-[(1E, 3E)-4-methoxycabutadienyl] thiophane of the Formula F A mixture of aldehyde 0.352 parts (1 mmol part) and phosphorane 0.432 parts (1.2 mmol part) in dichloromethane (5 parts) was stirred for 12 hrs. Removal of the solvent and chromatography ($SiO_2$) of the residue furnished ester of the Formula F 0.386 parts (89%) $[\alpha] = +85.51$ c = 1.160 (MeOH).

EXAMPLE 6

Pentanoic acid, 5-[Hexahydro-2-oxo-1,3-dibenzyl-4H-thieno (3,4-d) imidazol 3,5-dienyl]of the Formula G where R=hydrogen To a solution of ester 334 parts (1 mmol part) in MeOH (5 parts) was added 1 M NaOH (5 parts) and the reaction mixture was stirred for 3 hrs and left at 0° C. for 12 hrs. MeOH was removed under reduced pressure Water (5 parts) was added followed by 1 N HCl. Extraction of the aqueous solution b dichloromethane furnished the acid of the Formula G where R=hydrogen 310 parts (97%) $[\alpha] + 210.41$ c=0.48 (MeOH).

EXAMPLE 7

1H Thieno (3,4-d)-imidazol-4-pentanoic acid hexahydro-2-oxo-1,3-dibenzyl). 3aS-(3aα,4B, 6aα) of the Formula H where R=hydrogen acid of the Formula G where $R^2$=hydrogen 320 parts (0.1 mmol part) was dissolved in methanol (5 parts) and the solution was hydrogenated (3 atm) in the presence of 10% Pd/C (150 mg) for 8 hrs. Catalyst was filtered and removal of solvent under reduced pressure and purification of the residue (SiO$_2$) using 5% EtOAc-pet ether furnished 310 parts (96%) of the desired acid of the formula H where R$^2$ = hydrogen [α]$_D$ = −39.16 c=0.24 (MeOH).

EXAMPLE 8

Pentanoic acid, 5-[Hexahydro-2-oxo-1,3-dibenzyl-4H thieno (3,4-d) imidazol 3,5-dienyl], methyl ester of the Formula G where R$^2$=CH$_3$ To a solution of ester of the Formula F 0.434 parts (1 mmol part) in dichloromethane (5 parts) was added DBU 0.152 parts (1 mmol part) and stirred for 12 hrs. Removal of the solvent and purification of the residue by chromatography (SiO$_2$) using 25% EtOAc-pet ether furnished (0.326 parts, 75%) the deconjugated ester of the Formula G where a=CH$_3$.

EXAMPLE 9

1H Thieno (3,4-d)-imidazol-4-pentanoic acid hexahydro-2-oxo-1, 3-dibenzyl, methyl ester. 3aS-(3aα, 4B, 6aα) of the Formula H where R=CH$_3$ A solution of ester of the Formula G where R$^2$=CH$_3$ 0.438 parts (1 mmol part) 10% Pd on charcoal (20 mg) in methanol (10 parts) was hydrogenated at 3 atm. for 4 hrs. Filtration of the catalyst and removal of the solvent under reduced pressure furnished a residue which was purified by chromatography (SiO$_2$) to furnish compound of the Formula H where R$^2$=CH$_3$ in 0.420 parts (96%) [α] = −4.05 c=0.38 (CHCl$_3$).

EXAMPLE 10

1H Thieno (3,4-d)-imidazol-4-pentanoic acid hexahydro-2-oxo methyl ester 3aS-(3aα, 4B, 6aα). [D(+) BIOTIN METHYL ESTER] of the formula I where R$^2$=CH$_3$ Ester 0.438 parts (1 mmol part) was refluxed with 48% aq. HBr (20 parts) and methanol (1 part) for 6 hrs. Removal of the water furnished a residue (vacuum dried) The residue was taken in methanol (10 parts) and refluxed for 2 hrs in the presence of con. H$_2$SO$_4$(1 drop). Neutralization with NaHCO$_3$ and removal of methanol furnished a residue which was extracted with ethylacetate to furnish a residue which on purification by chromatography (SiO$_2$) using 75% EtoAc-pet ether furnished biotin methyl ester of the Formula I where R$^2$=CH$_3$ 0.206 parts (80% [α]$_D$=+83.75 c=0.4 (MeOH).

We claim:

1. A process for synthesis of D(+) biotin or the methyl ester thereof of Formula I:

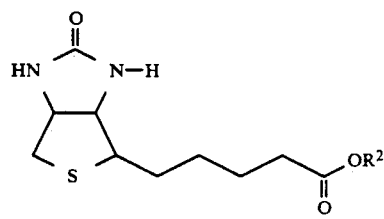

where R$^2$ is hydrogen or methyl which comprises
(a) reducing a lactol of Formula A:

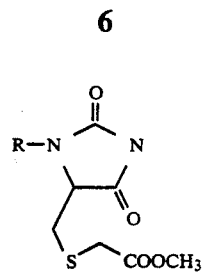

wherein each of R and R$^1$ is benzyl to produce a compound of Formula B:

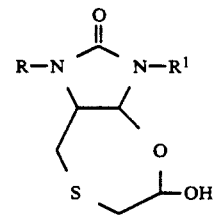

wherein R and R$^1$ are defined above,
(b) effecting ring opening of the oxathiepin ring of the compound of Formula B and protecting the 5 position of the imidazoline ring to produce a 5-protected-4-(formylmethyl thiomethyl)-1,3-dibenzyl imidazolid-2-one,
(c) converting the product of step (b) to the corresponding silyl enol ether by reaction with a siltation agent,
(d) cyclising the product of step (c) in the presence of methylene chloride and P-nitro benzaldehyde and a Lewis acid to produce a tetra hydro thiophene aldehyde of the formula:

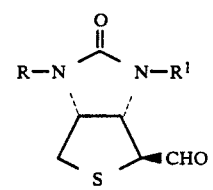

wherein R and R$^1$ are as defined above,
(e) treating said tetra hydro thiophene aldehyde with 3-(methoxy carbonyl-2-propenylidene) triphenyl phosphorane to produce a compound of Formula F:

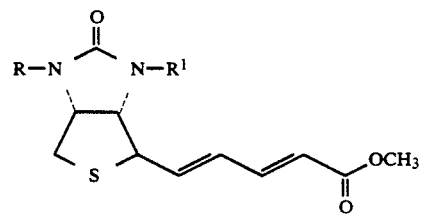

(f) if desired in order to produce a compound of Formula I wherein R$_2$ is hydrogen, hydrolysing the product of step (e) to produce:

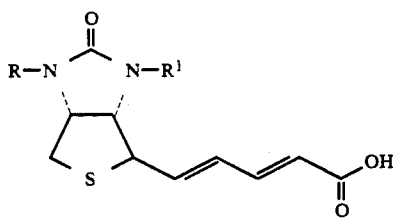

(g) Deconjugating the product of step (e) or, if effected step, (f) by reaction with lithium diisopropylamide, NaOH, alkali metal alkoxide or KOH to produce a compound of Formula G:

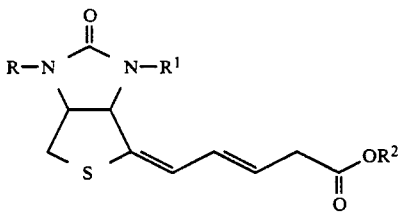

wherein $R_2$ is hydrogen or methyl (h) catalytically hydrogenating the product of step (g) using Pearlman's catalyst to produce a compound of the Formula H:

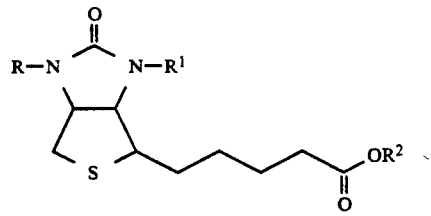

wherein R, $R^1$ and $R_2$ are as defined above and (i) Deprotecting the compound produced in step (h) by removal of the benzyl groups R and $R_1$ to produce the compound of Formula I.

2. A process according to claim 1 wherein steps a)–i) are carried out at room temperature.

3. A process according to claim 1 wherein diisobutylaluminumhydride is used to reduce the compound of Formula A to the compound of Formula B.

4. A process according to claim 1 wherein step b) is effected in the presence of thiophenol and a reagent selected from the group consisting of para-toluene sulfonic acid, 10-camphor sulfonic acid and benzene sulfonic acid.

5. A process according to claim 1 wherein aqueous HBr or metal/$NH_3$ is used to deprotect the compound of Formula H.

6. A process according to claim 1 where the Levis acid employed in step (d) is selected from the group consisting of $BF_3$, $EtO_2$, silver acetate, silver trifluoromethanesulfonate, $SnCl_4$, $AlCl_3$, trimethylsilyl trifluoromethanesulfonate and tert-butyl dimethyl silyl trifluoromethanesulfonate.

7. A process according to claim 1 wherein chlorotrimethyl silane, tert-butyldimethylsilylchloride or tert-butyldimethylsilyl trifluoromethanesulfonate is used to convert the product of step (b) to its corresponding silyl enol ether.

* * * * *